(12) United States Patent
Israel

(10) Patent No.: US 6,440,070 B2
(45) Date of Patent: Aug. 27, 2002

(54) INTRAOCULAR PRESSURE MEASUREMENT

(75) Inventor: Henry Israel, Bnei Brak (IL)

(73) Assignee: Ness Tec Ophthalmic Systems Ltd., Or Yehuda (IL)

( * ) Notice: Subject to any disclaimer, the term of this patent is extended or adjusted under 35 U.S.C. 154(b) by 0 days.

(21) Appl. No.: 09/849,407

(22) Filed: May 7, 2001

Related U.S. Application Data

(60) Provisional application No. 60/202,648, filed on May 8, 2000.

(51) Int. Cl.[7] ................................................. A61B 3/16
(52) U.S. Cl. ..................................................... 600/398
(58) Field of Search ................................. 600/398, 401, 600/405, 558

(56) References Cited

U.S. PATENT DOCUMENTS

| | | | |
|---|---|---|---|
| 3,070,997 A | | 1/1963 | Papritz et al. |
| 4,621,644 A | * | 11/1986 | Eilers ........................... 128/652 |
| 5,396,888 A | * | 3/1995 | Massie et al. .............. 128/649 |
| 5,830,139 A | * | 11/1998 | Abreu ......................... 600/405 |
| 5,865,742 A | | 2/1999 | Massie |

* cited by examiner

Primary Examiner—Max Hindenburg
(74) Attorney, Agent, or Firm—Dekel Patent Ltd.

(57) ABSTRACT

Apparatus for measuring intra-ocular pressure of an eye includes a housing and a processor. The housing has a protuberance with a flat surface and the processor includes a distance-measuring unit and a force-measuring unit. Intra-ocular pressure is calculated based on force/distance relationships, where the distance includes a measurement to an internal element of the eye. The processor calculates intra-ocular pressure by determining a zero displacement pressure.

29 Claims, 6 Drawing Sheets

INTRAOCULAR PRESSURE MEASUREMENT

CROSS-REFERENCES TO OTHER APPLICATIONS

This application claims priority of U.S. Provisional Patent Application No. 60/202,648 filed on May 8, 2000, which is incorporated in its entirety by reference herein.

FIELD OF THE INVENTION

The present invention relates to medical diagnostic systems in general and specifically to non-invasive measurements of intra-ocular pressure.

BACKGROUND OF THE INVENTION

Glaucoma is a condition of optic nerve degeneration resulting in loss of vision, characterized by an elevation in intra-ocular pressure (IOP). If left untreated, severe loss of vision and eventual blindness may occur. Several methods of treatment, including medication, laser and surgical procedures are employed in combating this condition. The common goal of all the methods is to reduce the IOP so that vision loss is kept to a minimum.

In controlling glaucoma, it is necessary to closely monitor the IOP. This is generally accomplished in a physician's office, hospital or clinic at periodic visits. Several diagnostic systems are available for this purpose.

All of the diagnostic systems in use today are versions of a mechanical tonometer, which are based on direct pressure measurement, as shown in FIGS. 1A and 1B, to which reference is now made. FIG. 1A is a depiction of an eye 20 with a cornea 22 and lens 24. FIG. 1B is a depiction of eye 20 whose cornea 22 is flattened by a force F.

Defining pressure P as force F per area A (P=F/A), IOP is obtained, as shown in FIG. 1B, by applying force F to a planar surface 26 (in this case, a circular surface having a diameter D) against cornea 22 and measuring force F required to flatten cornea 22 to an area measured on the planar surface. Pressure P is then calculated as the ratio of force F to the determined area.

The general methods of measuring IOP are: a) to apply a force and measure the resulting flat area (either directly or indirectly by measurement of deflection and calculation of resulting area based on an assumed corneal radius) or b) to depress the cornea to attain a given diameter flat area, measure the required force and calculate the resulting pressure as force per unit area.

The most widely used mechanical tonometer is the Goldmann Applanation Tonometer, described in U.S. Pat. No. 3,070,997. The general to principle is that shown in FIG. 1B, of direct pressure measurement following applanation (or flattening) of cornea 22. A flattened diameter of 3.06-mm has been determined by experimental methods to be optimal for this method. The flat contact surface is chosen so that no component of corneal tension is perpendicular to the cornea tonometer interface. This method is considered the "Gold Standard" although it suffers inaccuracies due to variations in measurement caused by differences in corneal thickness and the angle of application of force F.

Other tonometers have been developed using the same principle of measuring force per flattened/indented area. Indentation tonometers follow the same general principle, but use weighted plungers, which usually result in greater displacements. Vertical movements of a plunger are correlated to values of IOP for particular applied forces. This is generally done using weights, as in the Schiotz Tonometer (available from, for example, Precision Optical Machine, Philadelphia Pa., USA), but it may also be done with springs. Alternatively, electronic indentation tonometers, such as the MacKay-Marg and the TonoPen (both available from Precision Optical Machine, Philadelphia, Pa., USA) have flat plungers that are sensitive to displacements of less than one micron.

Impression tonometers employ various weights with disks attached. The disks are inked with a dye and are used to indent the cornea. To measure the area of impression for different weights, the remaining dye is stamped onto a page and the diameter is measured. The Maklakov Tonometer (for example Barraquer 65/90-mm Hg Tonometer, Ocular Instruments, Inc., Bellevue, Wash., USA) is one example.

Non-contact tonometers have also been developed to avoid direct placement on the cornea. These tonometers cause a displacement either by a puff of air (U.S. Pat. No. 3,538,754), or by an acoustic beam (U.S. Pat. No. 5,865,742), rather than by mechanical means. The moment at which corneal flattening occurs may be sensed using a photoelectric means.

In all of these methods, there are many factors that contaminate the simple principle of IOP calculation, such as the following: (1) In flattening a corneal segment from a spherical surface to a plane, the volume of aqueous fluid under the dome is displaced and hence the IOP is increased. (2) Tear fluid fills the angle between the cornea and plane surface implying a larger corneal contact area than actually exists, which results in a lower IOP reading. (3) The surface tension of the tear meniscus adds another force to the applied force. (4) The cornea resists bending. (5) The corneal thickness and eye elasticity vary from individual to individual, which biases the pressure measurement. (6) The angle of force application is not measured, which biases the pressure measurement. (7) The corneal segment may be flat prior to the measurement due to an accident or medical intervention such as corneal sculpturing.

Regardless of the means of measuring the result of perturbing the cornea, the calculation method does not vary from system to system. Thus, inaccuracies and errors in calculation occur in all the existing devices.

Furthermore, the existing technology is not appropriate for a self-administered test. First and foremost, the present measurement devices measure directly on the cornea. Even non-contact tonometers require that the eye must be opened in order to perform the examination on the cornea, which, if performed improperly, may result in eye damage. Thus, the procedures cannot be safely administered at home.

SUMMARY OF THE INVENTION

There is provided, in accordance with an embodiment of the present invention, apparatus for measurement of intra-ocular pressure of an eye, including a distance-measuring unit and a processor. The distance-measuring unit measures a distance from an external surface of the eye to an internal element of the eye. The processor generates the intra-ocular pressure from at least the distance measurement.

There is provided, in accordance with another embodiment of the present invention, a non-invasive ocular pressure measuring unit, including a housing having a protuberance with a generally flat surface and a processor. The processor includes at least a force-measuring unit that measures a force applied by the protuberance to an eyelid.

There is provided, in accordance with another embodiment of the present invention, a method for detecting intra-ocular pressure of an eye, including the step of calculating a distance from an external surface of an eye to an internal element of the eye.

There is provided, in accordance with another embodiment of the present invention, a method for detecting intra-ocular pressure of an eye. The method includes placing an apparatus having a force-measuring unit against an eyelid, measuring a force resulting from the placement, and calculating an intra-ocular pressure from at least the force measurement.

There is provided, in accordance with another embodiment of the present invention, a method for correcting for material properties of an external element of an eye. The method includes the steps of measuring a force applied to the external element, measuring a distance from the external element to an internal element of the eye, and generating a value from a function relating the force and distance. The value relates to a zero displacement value of the function.

There is provided, in accordance with another embodiment of the present invention, a system for measurement of intra-ocular pressure of an eye. The system includes a housing with a protuberance with a generally flat surface and a processor. The processor includes a force measuring unit for measuring a force applied by the protuberance to an external surface of the eye, and a distance measuring unit for measuring a distance from the external surface of the eye to an internal element of the eye. The processor is configured to calculate a relationship between the force and distance measurements so as to produce a definable function of pressure over a range of values.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

The present invention is a device that generates an intra-ocular pressure (IOP) reading from an applied force F and a resulting distance X. Force F may be applied through the eyelid or directly on the cornea. Distance X may be measured from the end of the device, from the cornea of the eye, or from any other point external to the eye to any internal structure within the eye. Since the fluid within the eye is non-compressible and the elastic property of the eye is generally linear over the measurement ranges to be considered, there is a definable relationship between force F and distance X, which can be used to calculate IOP, as described in more detail hereinbelow.

Figure 1A:
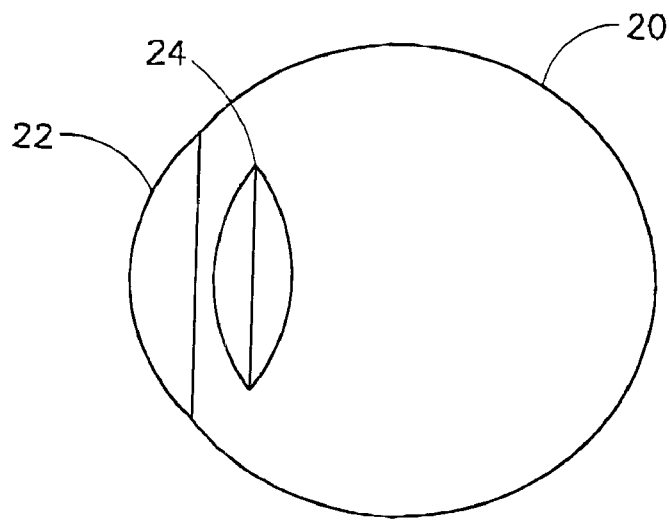
FIGS. 1A and 1B are schematic illustrations of an eye.
Figure 1B:
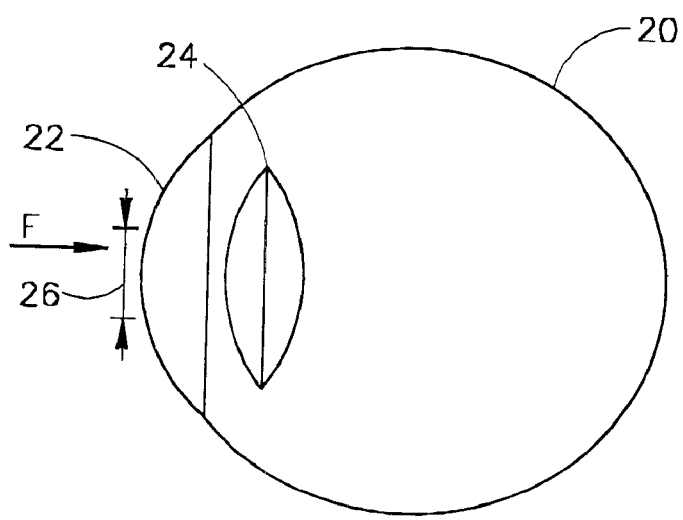
Figure 2A:
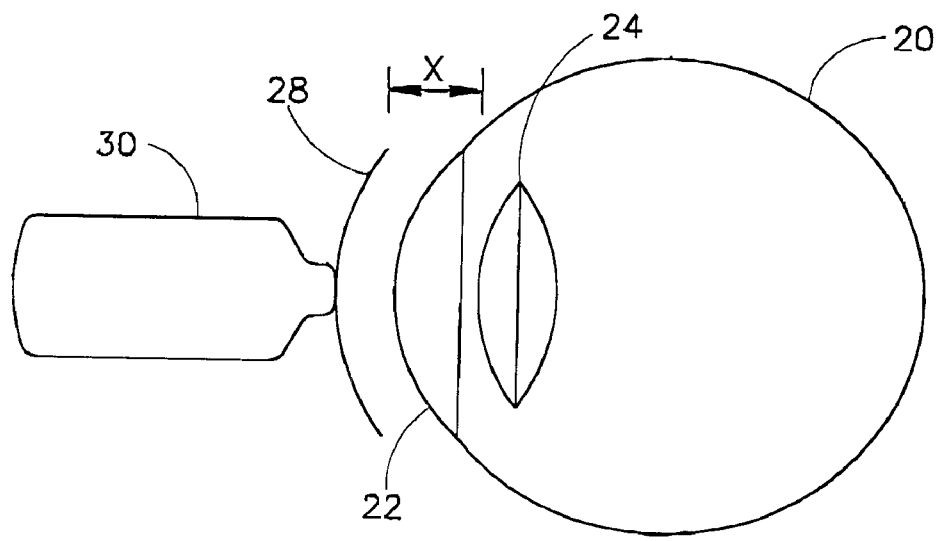
FIGS. 2A and 2B are schematic illustrations of one embodiment of the present invention before and during use.
Figure 2B:
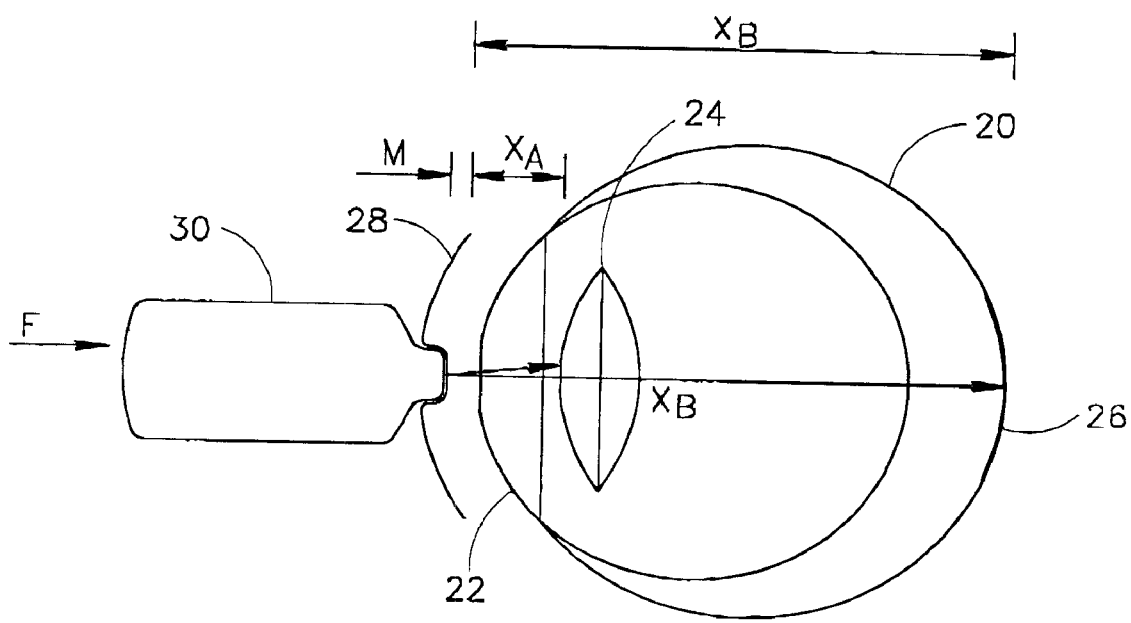

Reference is now made to FIGS. 2A and 2B, which are schematic illustrations of one embodiment of the present invention, a device generally referenced 30, placed over an eyelid 28. Previously introduced reference numerals refer to similar elements and will not be reintroduced.

FIG. 2A shows device 30 and eye 20 before the application of force F, and FIG. 2B shows device 30 and eye 20 after the application of force F. Prior to application of force F, as shown in FIG. 2A, cornea 22 is considered nearly spherical and in an equilibrium state. External forces acting on eye 20, such as air pressure and corneal hoop stress, are balanced against the IOP. This static IOP is the sought-after value.

When force F is applied, as in FIG. 2B, eyelid 28 is compressed until it becomes incompressible. Cornea 22 is flattened, and thus is displaced by an amount M. This causes relative movement of the cornea with respect to internal structures of eye 20. The amount of movement, in either the positive or the negative direction, can be described and measured as distance X. For example, distance $X_A$ between a lens 24 and cornea 22 may be measured, or distance $X_B$ of a retina 26 with respect to cornea 22 may be measured. Any internal structure may be used, relative to cornea 22, or to some other predetermined spot.

Distance X is measured via a distance-measuring unit. The distance measurement can be accomplished using any measurement device that will accurately measure the differential distance, such as an ultrasound transducer, a laser range finder or a mechanical scale. When a field based measurement device such as an ultrasound transducer or laser is used, it is preferable to use a narrow beam device to reduce the noise and spurious signals. An ultrasound device such as the Biometric Ruler (DB3000) (Ocuserv Instruments, New York, USA) or any equivalent "A" scan device may be used.

The force can be measured using a simple load cell with a single strain gauge or a suitable directional strain gauge array. Both the movement and force can be measured using direct mechanical means. However, it is more convenient to measure the motion and the force using a method that converts easily to a binary signal that is computer compatible. An example of a force-measuring device is the force gauge, for example, the EG Series manufactured by Mark-10, New York, USA. The relationship between distance X and force F are used to calculate IOP, as described hereinbelow.

Figure 3A:
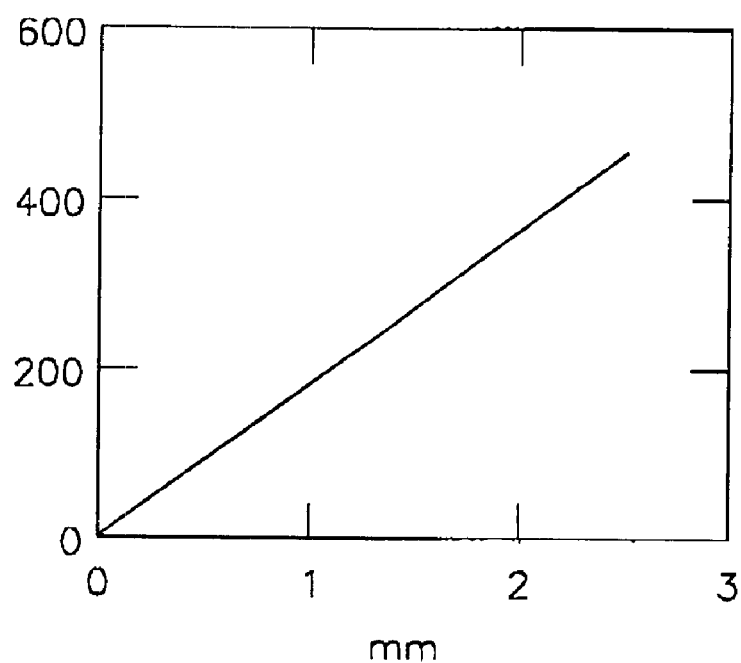
FIGS. 3A and 3B are graphical illustrations of force and pressure curves for one embodiment of the present invention.
Figure 3B:
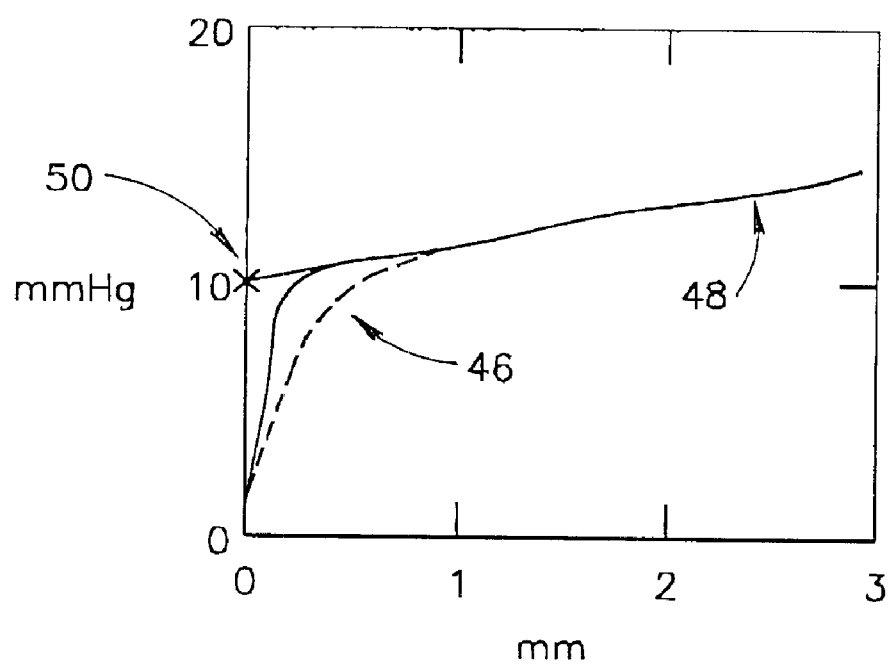

Reference is now made to FIGS. 3A and 3B, which are graphical illustrations of force and pressure curves, useful in understanding the calculation of IOP using device 30. The graphs were produced for illustrative purposes by a computerized mechanical simulation of the eye, simulating the eye as a volume of incompressible fluid in an elastic container, based on a model describing the average elastic response of the whole eye by Richard Collins, "Fluid Dynamics of the Eye", in *Applied Physiological Mechanics*, Edited by Dhanjoo N. Ghista; 1980; pp. 697–729; Harwood Academic Publishers; ISBN 3-7186-0013-7, incorporated herein by reference. In the present model, a compressible connection has been added to simulate the effect of making the measurement through the eyelid. As seen below, measuring through the eyelid has no effect on the final value.

FIG. 3A is a graphical illustration of a force curve. Force F is depicted on the y-axis, in normalized units, and distance X is depicted on the x-axis, in mm. The plot is an increasing linear curve, denoting that force F is increased linearly over the given range of distances X.

FIG. 3B is a graphical illustration of calculated pressure P, measured through eyelid 28. Pressure P is depicted on the y-axis, in mm Hg and distance X is depicted on the x-axis, in mm. Pressure P is calculated as force F per area A. Area A is the area of a cross-section of applied force F on eye 20. It should be noted that when calculations are done using device 30, rather than using a mechanical simulation, area A is a predetermined value based on the shape of device 30. As force F is increased linearly over the range of distances X, as depicted in FIG. 3A, pressure P changes according to the curves shown in FIG. 3B.

Two separate models were used, one mimicking a thin eyelid 28, shown as a solid line, and one mimicking a thick eyelid 28, shown as a dotted line. In both cases, there is an initial nonlinear segment 46 to the curve, corresponding to compression of the eyelid. Nonlinear segment 46 is longer for the thick eyelid (dotted line) than for the thin eyelid (solid line). However, once the eyelid reaches incompressibility, the relationship is linear in either case, as shown on the graph and referenced 48. Linear portion 48 of the curve corresponds to the elastic properties of eye 20, which has a nearly linear constant of elasticity. Thus, linear portion 48 of the curve is the same for both eyelids. Since this portion of the curve is used to calculate IOP, differences in material and mechanical characteristics of eyelids 28 generally have little or no effect on the final calculation of IOP.

A Least Mean Square fit to the data over the linear portion produces an average slope, and solution for a y-intercept 50 (or zero-displacement intercept) of that slope gives the zero displacement pressure, i.e. the IOP. That is, $$P(t)=m*X(t)+P(0)$$

where P(t) is the pressure at a given time t, and X(t) is the distance at the same time t. The value of the slope, m, is generated from the curve. P(0) is the static pressure, which is the IOP. By solving the equation for P(0), IOP is obtained. For example, in FIG. 3B, the resulting IOP would be approximately 10 mm Hg. The resulting value for IOP is generally without measurement perturbation or errors caused by compression of eyelid 28.

Alternatively, the zero displacement pressure may be calculated by producing a table of values for force and pressure during positive and negative displacement of the eyelid. The value for intra-ocular pressure can be determined as the pressure just before the force reaches zero during negative displacement.

In another embodiment, device 30 can be placed directly over cornea 22, as in the prior art systems. Calculation of IOP when placed over cornea 22 would be similar to calculation of IOP when placed over eyelid 28, as described hereinbelow.

Figure 4A:
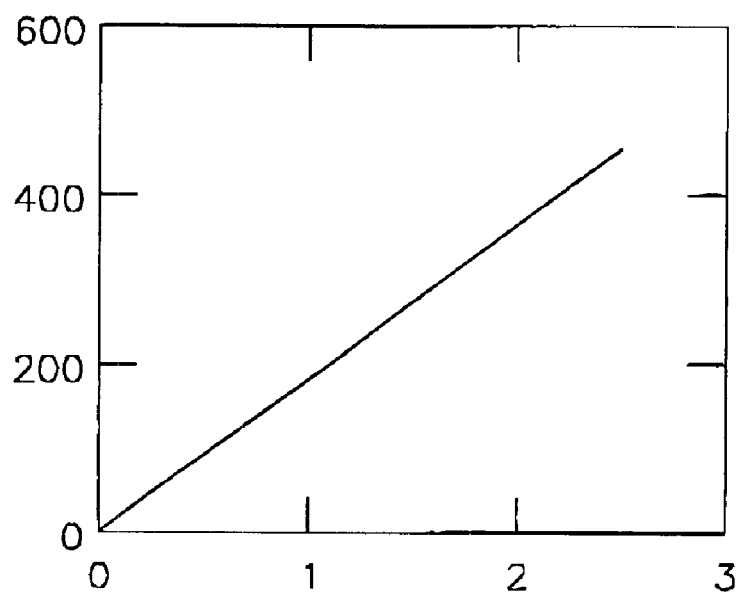
FIGS. 4A and 4B are graphical illustrations of force and pressure curves for another embodiment of the present invention.
Figure 4B:
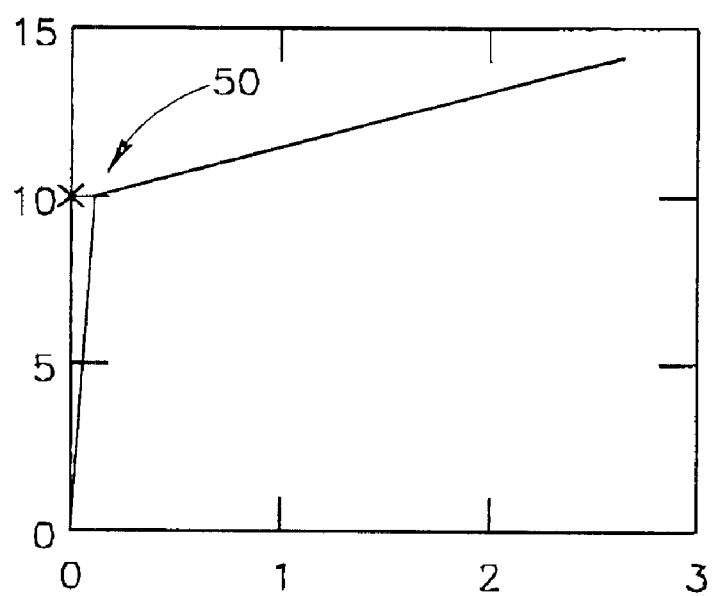

Reference is now made to FIGS. 4A and 4B which are graphical illustrations of force and pressure curves, useful in understanding the operation of device 30 when applied directly to cornea 22. A mathematical model was used as described above. FIG. 4A is a graphical illustration of a force curve. Force F is depicted on the y-axis, in normalized units, and distance X is depicted on the x-axis, in mm. The plot is an increasing linear curve, denoting that force F increased linearly over the range of distances X.

FIG. 4B is a graphical illustration of pressure P calculated from measurements taken at cornea 22. Pressure P is depicted on the y-axis, in mm Hg and distance X is depicted on the x-axis, in mm. Pressure P is calculated as force F per area A, as above. As force F is increased linearly, as depicted in FIG. 4A, pressure P changes according to the curve shown in FIG. 4B.

Solving for y-intercept 50 of the linear portion of the curve yields a result for IOP of 10 mm Hg, which is approximately the same value obtained for IOP in the previous embodiment. Thus, differences in eyelid and cornea response are generally removed by this method. In applications where it is desired to measure directly on the cornea, the non-linear portion of the data becomes small and an actual curve fit may not be needed. In that case, the force used in calculating the intra-ocular pressure is taken as the force at zero displacement.

Figure 5:
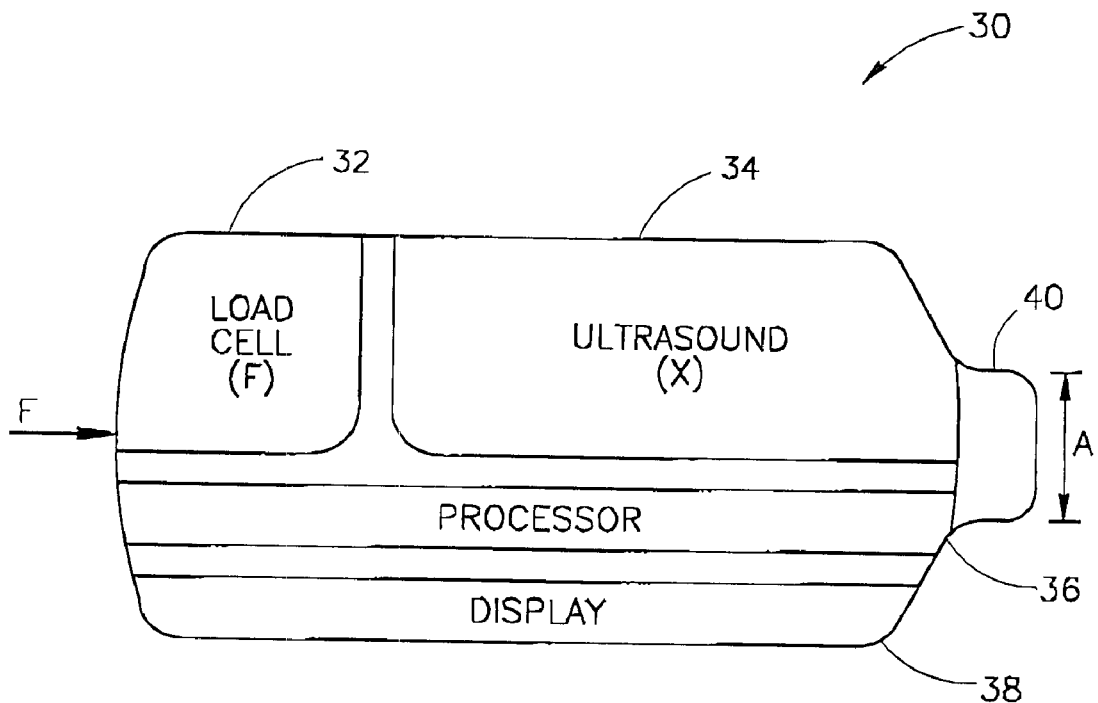
FIG. 5 is a schematic illustration of one embodiment of the present invention.

Reference is now made to FIG. 5. FIG. 5 is a schematic illustration of one embodiment of the present invention. As shown in FIG. 5, device 30 is a portable, hand-held unit, with a load-cell 32, an ultrasound measurement system 34, a processor 36 and a display 38. A protuberance 40 is positioned at one end. Load-cell 32, which measures applied force F, and ultrasound measurement system 34, which measures resulting distance X, are connected in parallel to processor 36. Processor 36 is connected to display 38. As device 30 is placed against eye 20, with the entire area A of protuberance 40 in contact with eye 20, data collection begins.

Figure 6:
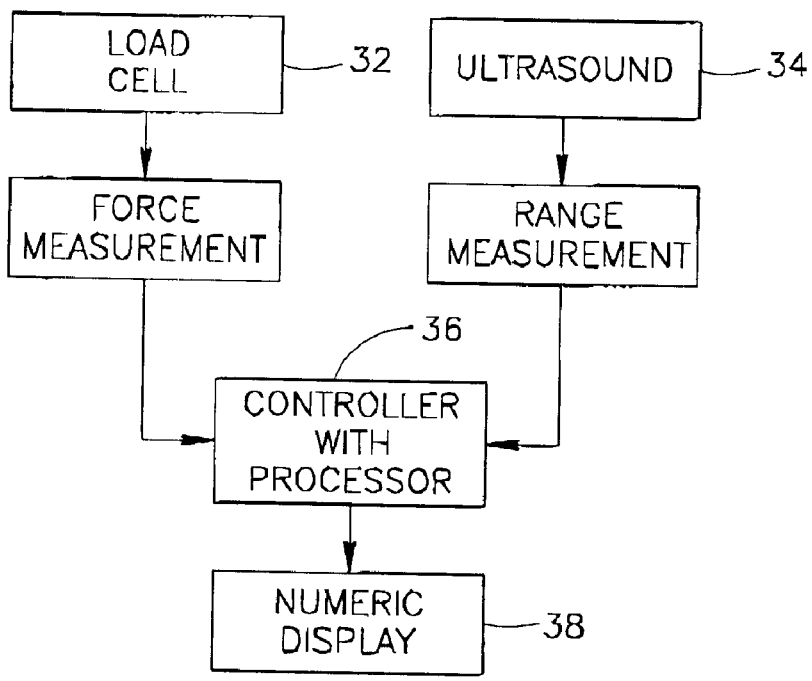
FIG. 6 is a hardware block diagram showing one embodiment of the present invention.

Reference is now made to FIG. 6. FIG. 6 is a block diagram illustration showing the operation of device 30 as depicted in FIG. 5. Force data are sent to processor 36 from load-cell 32, and distance data are sent to processor 36 from ultrasound measurement system 34. Force data are converted into pressure data by dividing by the area of contact, that is, the area of protuberance 40. Processor 36 uses this information to calculate the static IOP according to the above process, and this value is projected numerically on display 38.

Figure 7:
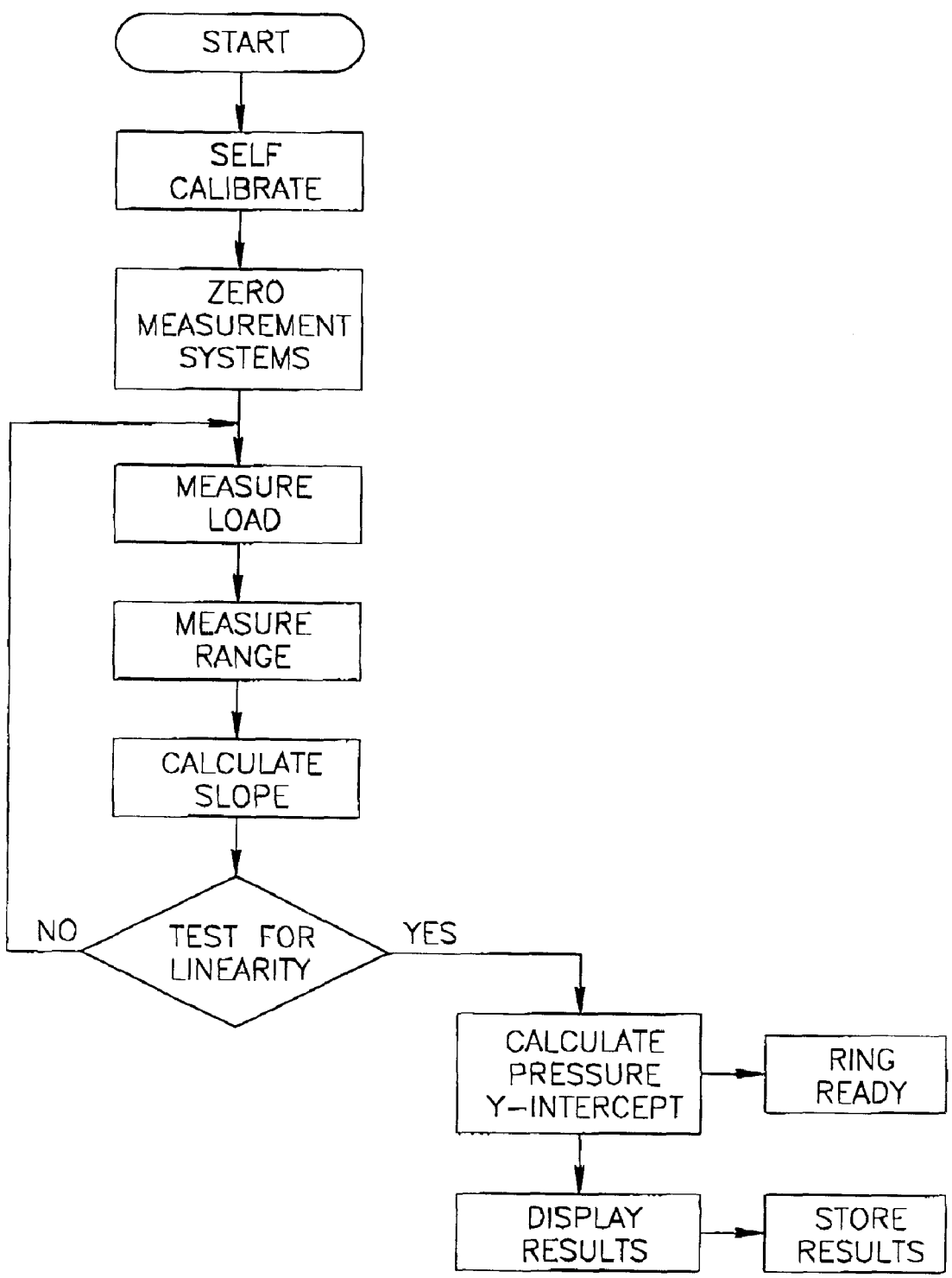
FIG. 7 is a flow chart illustration of a method of calculation and display.

Reference is now made to FIG. 7, which depicts a system flow diagram. The apparatus first goes through a self-calibration cycle, and the baseline is set to zero. The force F is measured continuously, even prior to contact with eyelid 28 (or cornea 22), in order to establish a zero base line. At the detection of a distance change, the system goes into a coordinated loop in which distance and load pairs are measured. The slope of these pairs is calculated and tested for linearity. When the pressure to distance relationship becomes linear, the test criterion is passed, and the coordinated loop stops. At this point, the zero displacement intercept of the linear curve is calculated, giving the IOP value. Once the IOP value is obtained, an alarm rings and the value is displayed and stored. In the fault case of a time out or measurement fault, a different alarm is sounded and an error message is displayed. Several features such as a remote computer interface and data storage (not shown) may be included in the software to aid in data collation.

It will be appreciated by persons skilled in the art that the present invention is not limited by what has been particularly shown and described hereinabove. Rather the scope of the invention is defined by the claims that follow:

What is claimed is:

1. Apparatus for measurement of intra-ocular pressure of an eye, the apparatus comprising:
   a distance-measuring unit for measuring a distance from an external surface of said eye to an internal element of said eye; and
   a processor for generating said intra-ocular pressure from at least said distance measurement.

2. The apparatus of claim 1 wherein said distance-measuring unit is an ultrasound transducer.

3. The apparatus of claim 1 wherein said distance-measuring unit is a laser.

4. The apparatus of claim 1 wherein said external surface is selected from the group consisting of an eyelid and a cornea.

5. The apparatus of claim 1 wherein said internal element is selected from the group consisting of a lens and a retina.

6. The apparatus of claim 1 wherein said processor is configured to generate said intra-ocular pressure by calculation of a zero displacement value.

7. The apparatus of claim 1 wherein said processor comprises a force measuring unit, and wherein said intra-ocular pressure is generated from said distance measurement and a force measurement.

8. A non-invasive ocular pressure measuring unit comprising:
   a housing having a protuberance with a generally flat surface; and
   a processor comprising at least a force-measuring unit, for measuring a force applied by said protuberance to an eyelid.

9. The unit of claim 8, wherein said processor further comprises a distance measuring unit, for measuring a distance from said eyelid to an internal element of an eye.

10. The unit of claim 9 wherein said distance-measuring unit is selected from the group consisting of an ultrasound transducer and a laser.

11. The unit of claim 8 wherein said force-measuring unit is a load cell.

12. A method for detecting intra-ocular pressure of an eye, the method comprising the steps of:
   measuring a distance from an external surface of an eye to an internal element of an eye; and
   calculating said intra-ocular pressure from said distance.

13. The method of claim 12, wherein said external surface is selected from the group consisting of an eyelid and a cornea.

14. The method of claim 12 wherein said internal element is selected from the group consisting of a lens and a retina.

15. A method for detecting intra-ocular pressure of an eye, the method comprising the steps of:
   having an apparatus placed against an eyelid, wherein said apparatus comprises at least a force-measuring unit;
   measuring at least a force resulting from said placement; and
   calculating an intra-ocular pressure from said at least force measurement.

16. The method of claim 15, wherein said step of measuring at least a force further comprises measuring a distance from said eyelid to an internal element of said eye, and wherein said step of calculating comprises calculating an intra-ocular pressure from said distance measurement.

17. The method of claim 16, wherein said step of calculating comprises the steps of:
   determining a function for pressure relating said force measurements to said distance measurements; and
   calculating a value for intra-ocular pressure based on said function at zero displacement.

18. A method for correcting for material properties of an external element of an eye, the method comprising the steps of:
   measuring a force applied to said external element;
   measuring a distance from said external element to an internal element of said eye; and
   generating a zero displacement value from a function relating said force and said distance.

19. The method of claim 18 wherein said external element is selected from the group consisting of an eyelid and a cornea.

20. The method of claim 18, wherein said internal element is selected from the group consisting of a lens and a retina.

21. The method of claim 18 wherein said function comprises a linear segment.

22. The method of claim 18 wherein said value is a pressure value.

23. The method of claim 18, wherein said material properties are selected from the group consisting of compressibility, thickness and elasticity.

24. A system for measurement of intra-ocular pressure of an eye, the system comprising:
   a housing having a protuberance with a generally flat surface; and
   a processor, said processor comprising:
      a force measuring unit for measuring a force applied by said protuberance to an external surface of said eye; and
      a distance measuring unit for measuring a distance from said external surface of said eye to an internal element of said eye,
   wherein said processor is configured to calculate a relationship between said force and distance measurements so as to produce a definable function of pressure over a range of values.

25. The system of claim 24, wherein said external surface is selected from the group consisting of an eyelid and a cornea.

26. The system of claim 24, wherein said internal element is selected from the group consisting of a lens and a retina.

27. The system of claim 24, wherein said definable function includes a linear portion.

28. The system of claim 24 wherein said distance measuring unit is selected from the group consisting of an ultrasound transducer and a laser.

29. The system of claim 24 wherein said force measuring unit is a load cell.

* * * * *